US006689569B2

(12) United States Patent
Vojdani

(10) Patent No.: US 6,689,569 B2
(45) Date of Patent: Feb. 10, 2004

(54) SALIVA TEST FOR DETECTION OF FOOD ALLERGY, CANDIDIASIS, MICROFLORA IMBALANCE, INTESTINAL BARRIER DYSFUNCTION AND HUMORAL IMMUNODEFICIENCIES

(75) Inventor: Aristo Vojdani, Los Angeles, CA (US)

(73) Assignee: Immunosciences Lab., Inc., Beverly Hills, CA (US)

( * ) Notice: Subject to any disclaimer, the term of this patent is extended or adjusted under 35 U.S.C. 154(b) by 149 days.

(21) Appl. No.: 09/930,785

(22) Filed: Aug. 14, 2001

(65) Prior Publication Data

US 2003/0087320 A1 May 8, 2003

(51) Int. Cl.[7] ...................... G01N 33/53; G01N 33/567; G01N 33/569; G01N 33/566
(52) U.S. Cl. ...................... 435/7.2; 435/7.31; 435/7.33; 435/7.34; 435/7.35; 435/7.37; 436/501
(58) Field of Search ................................. 435/7.2, 7.31, 435/7.33, 7.34, 7.35, 7.37; 436/501

(56) References Cited

U.S. PATENT DOCUMENTS 5,420,014 A * 5/1995 Cripps et al.
6,103,480 A 8/2000 Vojdani

OTHER PUBLICATIONS

Husband, A.M., Gowans, "The Origin and Antigen–Dependent Distribution of IgA–Containing Cells in the Intestine." *J Exp. Med* 1978; 148:1146–60.

Kagnoff, M.F., "Effects of Antigen–Feeding on Intestinal and Systemic Immune Responses. I. Priming of Precursor Cytotoxic T Cells by Antigen Feeding." *J Immunol* 1978; 120: 395–399.

Mestecky, J., McGhee, J.R., Arnold, R.R., et al., "Selective Induction of an Immune Response in Human External Secretions by Ingestion of Bacterial Antigen." *J Clin Invest* 61:731–737, 1978.

Cunningham–Rundles, C., Brandeis, W. E., et al., "Bovine Antigens and the Formation of Circulating Immune Complexes in Selective Immunoglobulin A Deficiency." *J Clin Invest.* 64:272–279, 1979.

Brandtzaeg, P., "Transport Models for Secretory IgA and Secretory IgM." Clin Exp. Immunol. 44:221–232, 1981.

Concha, E., Subiza, J.L., et al., "Disorders of Regulatory T Cells in Patients With Selective IgA Deficiency and its Relationship to Associated Autoimmune Phemomena." *Clin Exp. Immunol.* 49:410–418, 1982.

Bienenstock, J., Befus, A.D., "Some Thoughts on the Biologic Role of Immunoglobulin A." *Gastroenterology.* 84:178–185, 1983.

Romero–Piffiguer, Vucovich, P.R., and Riera, C.M., "Secretory IgA and Secretory Component in Women Affected by Recidivant Vaginal Candidiasis." *Mycopathologia* 91:165–170, 1985.

Stone, A.A., Cox, D.S., et al., "Secretory IgA as a Measure of Immunocompetence.", *J. Human Stress.* 13:136–140, 1987.

Epstein, M.M., Baumgarten, A., "The Usefulness of Routine Screening For Salivary Secretory Component." *J Allerg Clin Immunol.* 88:356–360, 1991.

Dack, G.M., et al., "Bacterial Activity in Different Levels of Intestine and in Isolated Segments of Small and Large Bowel in Monkeys and Dogs," *J. of Inf. Disc.*, vol. 54. pp. 204–220 (1934).

Donaldson, R.M., "Normal Bacterial Populations of the Intestine and Their Relation to Intestinal Function (Continued)", *New England Journal of Medicine*, vol. 270, pp. 994–999 (1964).

Dupont, C., et al., "Food Induced Alterations fo Intestinal Permeability in Children With Cow's Milk–Sensitive Enteropathy and Atopic Dermatitis,"*J. Ped. Gastroentero Nut.*, vol. 8, pp. 459–465 (1989).

Lunn, P.G., et al., "Automated Enzymatic Assays for the Determination of Intestinal Permeability Probes in Urine. 2. Mannitol," *Clinica Chimica Acta.*, vol. 183, pp. 163–170 (1989).

Majamaa, H., et al., "Evaluation of the Gut Mucosal Barrier: Evidence For Increased Antigen Transfer in Children With Atopic Eczema," *J. All Clin. Immunol.*,, vol. 97, pp. 985–990 (1996).

Marshall, J.C., et al., "Immunomodulation by Altered Gastrointestinal Tract Flora," *Arch. Surg.*, vol. 123, pp. 1465–1469 (1988).

Walker, W.A., et al., "Intestinal Antibodies," *New Engl. J. Med.*, vol. 297, pp. 767–773 (1977).

Challacombe, S.J., "The Induction of Secretory IgA Responses in: food allergy and intolerance", edited by Brostoff J., Challacombe, S.J., published by W.B. Sanders Eastbourne, England (1987) Chapter 15, pp. 269–285.

* cited by examiner

Primary Examiner—Mark Navarro
(74) Attorney, Agent, or Firm—Knobbe, Martens, Olson & Bear, LLP

(57) ABSTRACT

A method for determining a cause for digestive and immune disorders is disclosed. The method determines the levels of antibodies against normal intestinal microflora and food antigens. It then compares the results to normal levels to determine the cause. The test can be used to diagnose food allergy or intolerance, microflora imbalance, gut barrier dysfunction, bacterial translocation, immunodeficiencies, candidiasis and autoimmunities.

18 Claims, 9 Drawing Sheets

SALIVA TEST FOR DETECTION OF FOOD ALLERGY, CANDIDIASIS, MICROFLORA IMBALANCE, INTESTINAL BARRIER DYSFUNCTION AND HUMORAL IMMUNODEFICIENCIES

BACKGROUND OF THE INVENTION

It is increasingly evident that human diseases are most often related to lifestyle and should in theory be preventable. The stress of modem life, our reduced physical activity, and our consumption of manipulated and processed foods, and of chemicals—including pharmaceuticals—all contribute to our decreasing resistance to disease. Much evidence supports the fact that our genes, adapted during millions of years to the lifestyle of our prehistoric ancestors, tolerate poorly the dramatic changes in lifestyle that have occurred, especially in food habits during the past 100 years. Changes in food habits in Western countries that no doubt constitute stresses to the human body and that may predispose to inflammatory, infectious, ulcerative, degenerative, and neoplastic diseases include the following: the consumption of 100 lb. refined sugar per individual per year; the 10-fold increase in sodium consumption; the fourfold increase in consumption of saturated fat; the doubled consumption of cholesterol; a much reduced consumption of vegetable fibres, and of minerals such as potassium, magnesium, calcium, and chromium; and a considerable reduction in consumption of omega-3 fats, membrane lipids, vitamins, and antioxidants. In severe disease, important food ingredients, such as arginine, glutamine, taurine, nucleic acids, vitamins, and antioxidants, such as glutathione, are often not supplied in large enough quantities.

Perhaps, even more important than the decrease in these food ingredients is the fact that prehistoric food contained several thousand times more bacteria, mainly the so called probiotic bacteria. Prehistoric methods of food preservation were either drying or, more commonly, storing in holes dug into the ground, where the food became naturally fermented. This is how Stone Age man learned to produce most of our still common fermented foods, such as beer, wine, green olives, and sauerkraut. Our modern lifestyle has dramatically reduced the availability of foods produced by natural fermentation. After the early identification of microbes, bacteria were regarded mainly as a source of disease, and unwanted in commercially manufactured food. Furthermore, the desire of the food industry to prolong shelf life promoted alternative production methods, such as the use of enzymes instead of live bacteria. With extensive hygiene measures practiced during delivery and in childcare, children in Western societies may have difficulty developing a satisfactory protective indigenous gut flora. It is not known, but suspected, that this could be connected to the increasing incidence of allergies and infections seen among Western children. A series of studies were published about an ethnic group in New Guinea with a dramatically different diet to that of people in the Western world. This diet contained no processed foods like butter, margarine, lard, oils, refined sugar, or alcohol. Instead, the group's diet was rich in fibre, water, vitamins, minerals, and omega-3 fats, such as docosahexaenoic acid (DHA) and eicosapentaenoic acid (EPA). Despite the fact that about 80% of the population smokes and has a heavy consumption of saturated fat from coconut, cerebrocardiovascular diseases are virtually absent and the incidence of diabetes and cancer is very low.

The Gastrointestinal Tract—the Port of Infectious Diseases

The condition and function of the gastrointestinal (GI) tract are essential to our well-being. After the respiratory tract, the GI tract constitutes the second largest body surface area, described to be somewhere between 250 and 400 $m^2$, or comparable in size to a tennis court. During a normal lifetime, 60 tons of food pass through this canal, which is important for well being, but also constitutes an enormous threat to the integrity of the digestive tract and the whole body. It is not surprising, therefore, that this organ is often affected by inflammatory diseases and cancer. The continuous challenges to the GI surfaces might be why most of the surface cells have a rapid turnover; most are replaced after three to four days in man and sometimes earlier in animals. Furthermore, the surface is protected by large quantities of important secretions, from saliva in the oral cavity to colonic secretion in the large bowel. These secretions contain factors of great importance for the lubrication of the mucosa and for functions of the GI tract, but also hundreds of ingredients of importance for intraluminal microbial defense. The secretory functions are extremely sensitive to foreign chemicals. About 50% of the 2000 pharmaceutical drugs registered in Sweden have reported GI side effects, for example, mouth dryness, nausea, vomiting, diarrhea, and constipation. It is hoped that future medicine will be more restrictive in the use of pharmaceuticals in general and will use drugs with as few side effects as possible.

Stress and Nutritional and Xenobiotic Influences of the GI Tract

Stress is known to affect the composition of the intestinal preventive flora. Infants fed on artificial infant formulas have, in contrast to breastfed ones, a very low degree of colonization with lactobacilli and bifidobacteria, but high counts in enterococci, coliforms, and clostridia. This may relate to excessive hygiene measures during delivery in Western countries, which prevent transfer of anaerobic microflora from mother to infant. It is also known that cosmonauts on return to Earth have lost their lactobacillus flora, especially *L. planatarum*, which is partly replaced by a higher intestinal content of PPMs, changes attributed to stress and poor eating. Also, xenobiotics (an exogenous agent, such as an environmental chemical not usually present in the body) in the diet can affect the contents of intestinal microflora.

In a recent observation, it was proposed that ulcerative colitis is induced by xenobiotic metabolites, damaging the colonic epithelial barrier and exposing the mucosal immune system to luminal contents. It is possible to account for all of these observations by proposing that ulcerative colitis is caused by a toxic metabolite of a xenobiotic which is excreted in bile and activated during its passage through the colon. Intermittent exposure to the parent compound would be a feature of the environment, possibly part of the diet, in areas where the disease is more common.

The genetic influence could be explained by inherited differences in the capacity of the hepatic enzymes responsible for its metabolism, resulting in decreased elimination of the parent compound by its usual pathway and increased transformation into the reactive metabolite. The most likely candidate enzymes are members of the cytochrome P450 superfamily of mixed-function oxidases, although genetic polymorphisms of other enzymes involved in xenobiotic metabolism have been described. Induction by smoking or inhibition by estrogen of the P450 enzymes involved in alternative metabolic pathways would affect the proportion of the parent compound transformed into the toxic metabolite. Reactive metabolites produced by this system are commonly coupled to an endogenous conjugate, such as glucuronic acid, before excretion into bile.

Bacteria in the gut have enzymes which can act on luminal substrates. In particular, bacterial β-glucuronidase and sulphatase are capable of hydrolysing the products of hepatic conjugation. If the xenobiotic metabolite were to be slowly reactivated by intestinal bacteria, its luminal concentration would rise with passage down the colon. Once the concentration became toxic, the colonic epithelial barrier would be breached, allowing the mucosal immune system to react to luminal contents distal to that point. In susceptible individuals, the biliary epithelium could also be damaged by the toxic metabolite, allowing presentation of biliary antigens to surrounding lymphocytes by cells carrying appropriate HLA molecules, thereby initiating an inflammatory response in the biliary tree.

Assessment of Intestinal Integrity

Imbalance of gut mucosa permeability is the origin of the intestinal integrity problem.

The development of the gastrointestinal tract in mammals is characterized by the integrated maturation of its many functions. Digestion and absorption of nutrients, the critical factor for survival, depends on the state of development of the gastrointestinal tract. As well as digesting, absorbing and eliminating, the gut acts as a barrier between the internal and external environment.

Control of macromolecular uptake is dependent on a number of factors present either within the intestinal lumen or on the intestinal mucosal surface. These factors include both non-immunological and immunological processes. Nonimmunological factors (intestinal flora, secretion, gastric barrier, peristaltic movement and live filtration) help to control the proliferation of microorganisms present in the gastrointestinal tract, aid in decreasing adherence of organisms to the gut surface and are important in limiting the available antigen mass that may otherwise overwhelm local immunological defense mechanisms and penetrate the mucosal barrier or enter the systemic circulation.

Mucosal immunological factors (secretory IgA, cell mediated immunity, other immunoglobulins), especially the common mucosal associated lymphoid tissue (MALT), is present at all epithelial surfaces that are in contact with the external environment. This is largely independent of the systemic immune response and is governed by antigenic stimuli at epithelial surfaces. A failure or abnormality in one of these mechanisms can result in symptoms such as anaphylaxis, rhinitis, and skin rashes which may be classified as food allergy or intolerance.

In normal conditions, factors within the intestinal lumen of the surface of epithelial cells and within the lamina propria combine to limit the access of antigens to systemic circulation. After macromolecular ingestion by the intestinal absorptive cells, most of the portion that escapes breakdown is transported out of the cell by an exocytic mechanism. Any interference with intracellular capacity to digest macromolecules could therefore result in an increased intestinal transport of molecules. A number of factors can affect the stability and ability of lysosomes. For example, high concentration of vitamin A, radiation, bacterial and fungal endotoxins and exotoxins can increase the ability of lysosomes, causing the rupture of lysosomal membranes in various cellular systems. On the other hand, corticosteroids stabilize the lysosomal membrane and can interfere with the normal digestive function of these intracellular organelles. Thus, inhibition of lysosomal function could in turn result in enhanced transport of intestinal antigens, by decreasing intracellular breakdown and increased immune response against bacterial antigens.

The basis for possible immune-mediated disease in these cases may be the increased uptake of intestinal pathogens or macromolecules, which can interact with the circulating antibody and complement a target organ to produce characteristic autoimmune response. Furthermore, patients with selective IgA deficiency have a greatly increased incidence of Coeliac disease compared with the normal population. This is undoubtedly due to an increased uptake of gluten or its breakdown products. In a similar manner, intestinal pathogens or their byproducts can penetrate the intestinal mucosa, resulting in a generalized malabsorption. Therefore, increased or decreased intake of macromolecules may result in pathological conditions.

Intestinal Barrier Function Test

Recently, there has been considerable interest in the concept of enhanced intestinal permeability and its possible role in the pathogenesis and pathophysiology of a variety of intestinal and extraintestinal disorders. Bacterial flora is greatly influenced by eating habits, and chemical contamination of the foods which plays a significant role in the integrity of intestinal mucosa.

Mucosal surfaces in mammals provide an extensive area for adhesion of a wide variety of microorganisms. Soon after birth, the mucosal surfaces of the upper respiratory tract, the intestinal tract, and the lower genital tract become colonized by a variety of bacteria and other microorganisms. Most of these organisms become established as the indigenous microflora or normal microflora by attachment of bacterial cell via specific adhesions to the complementary receptors on the host epithelial cell membrane.

During states of good health, all of the mucosal surfaces contain remarkable barriers against attachment of invading bacterial pathogens. But due to the typical western diet (chemical contamination of the food, increased dietary carbohydrates, usage of broad spectrum antibiotics, corticosteroid hormones and birth control pills), these barriers may break down and pathogenic bacteria may colonize large areas of the mucosal surfaces. From these colonized sites, pathogenic bacteria produce infectious diseases either by invading into deeper tissues or secreting antigens and/or toxins that damage local and distant tissues. This systemic translocation of enteric bacteria and endotoxin plays a major role in the development of abnormal systemic immunity, which may end with multiple organ failure.

The pathogenesis of bacterial infectious diseases arising from mucosal surfaces involves a number of distinct interactions between the host and the bacterial pathogen. Virulence factors (for example fimbriae) of the bacteria enable the microorganism to attach to and multiply on mucosal surfaces and to evade the defense mechanisms of the host. This observation could mean that the intestinal tract represents a potential site for the absorption of bacterial breakdown products, proteolytic and hydrolytic enzymes, as well as food antigens that normally exist in the intestinal lumen. Therefore, inhibition of microbial attachments to the epithelial cell receptors via competing molecules, such as lectins, polysaccharides and other nutritional factors is the best strategy for prevention of mucosal immune dysfunction.

Mucosal immunodeficiency is an additional factor, which may contribute to an enhanced macromolecular absorption. Secretory IgA is the predominant immunoglobulin present in intestinal secretions. This class of immunoglobulin acts to protect the intestinal bacteria, fungi, and viruses, as well as of antigenic and toxic macromolecules. It is therefore possible that, in the absence of secretory IgA, and/or microflora imbalance, ingested proteins are absorbed from the gut in increased amounts (FIG. 1).

Increased Food Antigens Transfer in Atopic Eczema

Abnormal intestinal antigen handling is the root cause of atopic eczema. Dietary antigens are macromolecules with a molecular weight in the range of 10,000 to 70,000 Daltons. They are absorbed across the epithelial layer by transcytosis along two functional pathways. The main degradative pathway entails lysosomal processing of the protein to smaller peptide fragments, and is important in host defense to diminish the antigen load. More than 90% of the protein internalized passes in this way. A minor pathway allows the transport of intact proteins, which results in antigen-specific immune responses. In health, paracellular leakage of macromolecules is not allowed because intact intercellular tight junctions maintain the macromolecular barrier. Consequently, in health, antigen transfer is well-controlled, and aberrant antigen absorption does not occur.

Determination of both intact and degraded antigen absorption are important because they can be affected separately and their clinical and immunologic consequences may be different. Antigen handling in the gut is associated with the generation of oral tolerance. There is evidence that during the absorption process antigens are subtly altered into tolerogenic form. In the immature gut, because of immature absorptive functions, antigen exposure may result in priming for immune responses instead of oral tolerance. Increased uptake of intact food antigens in the immature gut has been explained by increased binding of antigens to the microvillus membrane. Aberrant and excessive antigen absorption increases the antigen load, which may be harmful to the host. In a like manner, incomplete degradation may result in the generation of new antigenic epitopes.

It is not known whether altered antigen transfer is a primary or secondary phenomenon in atopic eczema. In food allergy or intolerance, disturbances in intestinal permeability and antigen transfer occur when an allergen comes into contact with the intestinal mucosa. It has previously been shown that in active cows' milk allergy with predominantly gastrointestinal symptoms, the absorption of both intact and degraded horseradish peroxidase (HRP) is increased in untreated cases, but after complete avoidance of cows' milk, HRP transport returns to normal.

These results show that the intestinal mucosa is an important organ of defense, providing a barrier against the antigens encountered by the enteric route. The barrier functions may be incompletely developed in early infancy, which may explain the peak prevalence of food allergies or intolerance in this age group. In attempts to correlate atopic eczema with impaired gut mucosal barrier functions, it is important to measure the intestinal permeability to a high molecular weight probe such as HRP rather than a low molecular weight probe such as that used in the lactulose-mannitol test. This recommendation is based on findings that low molecular weight probes suffer from high degrees of false positivity.

Bacterial and Food Antigens May Induce Autoimmune Disease

The proposed mechanisms by which viruses or bacteria may initiate autoimmunity is through sharing of a common antigenic determinant between a virus or other microorganism and a host cell component. Such shared epitopes can be thought of as a three-dimensional conformation site or a stretch of amino acids forming a peptide. Thus, an antiviral or bacterial immune response would recognize both the microorganism determinant and the shared host self antigen. These cross-reacting antibodies and immune cells generated by molecular mimicry may in large part be responsible for the presence of autoreactive antibodies and cells found in many infections in humans.

Similarly, epidemiological and ecological investigations suggest that early infant nutrition, particularly drinking cows' milk may induce autoimmunity leading to insulin-dependent diabetes mellitus (IDDM). A supporting hypothesis is of immunological cross-reactivity between a fragment of bovine serum albumin and a β-cell protein of 69,000 M (p69) because both cellular and humoral immune responses to bovine serum albumin have been reported in patients with IDDM which cross-react with p69.

Human and bovine β-casein share approximately 70% homology and sequence differences could be therefore responsible for the generation of an immune response if milk proteins are introduced within the first weeks of life when the intestine is permeable to proteins. Based on results in NOD mice and evidence that patients with IDDM have autoantibodies to β-caseins at the time of diagnosis, T-cell reactivity to β-casein was measured.

Proliferative response to β-casein reinforces the concept of this protein being involved in causing the disease as indicated by the recent report of autoantibodies to β-casein in these patients. This finding is specific for patients with IDDM because no lymphocyte proliferation to β-casein was observed with cells from patients affected by autoimmune thyroid disease. A proliferative response to β-casein in patients with IDDM in childhood and as young adults suggests that this response has pathogenic relevance regardless of the age of onset of the disease. This data together with evidence deriving from experimental studies in the NOD mice, and the observation that a high percentage of IDDM patients has antibody to β-casein indicate β-casein as a good candidate milk protein related to IDDM.

It was concluded that the association between IDDM and early consumption of cows' milk may be explained by the generation of a specific immune response to β-casein. Exposure to cows' milk triggers a cellular and humoral anti-β-casein immune response, which may cross-react with a β-cell antigen. It is of interest that sequence homologies exist between β-casein and several β-cell molecules.

For this reason, measurement of saliva IgA, IgG, and IgM antibodies against specific antigens of foods, intestinal bacterial and fungal flora is of considerable importance in the pathogenesis of immunologically mediated diseases, including food allergies or intolerance and autoimmunities.

The mucosal tissues of the body provide an extensive surface on which potentially pathogenic microorganisms make their initial contact with the host. A variety of mechanism, including both immune and non-immune factors, have evolved to prevent colonization, invasion, and local disease. Predominant among the immune mechanisms is the occurrence of secretory antibodies in the fluids that bathe mucosal membranes. These antibodies have critical biological and medical implications because they interact with a large variety of viable and nonviable substances that are deposited on mucous surfaces.

Secretory IgA is capable of functioning as a blocking antibody, which can create a barrier to certain macromolecules, bacteria, and viruses. The interaction with secretory IgA will not permit such antigens to interact with the mucosa and blocks their entrance and exposure to the gut-associated lymphoid tissue. This blockage permits the host to shield efficiently the systemic immune response, local immune response, or both, from being bombarded by many molecules.

The properties of human IgA in serum and saliva are completely different. Serum IgA is monomeric and contains 80–90% $IgA_1$ and 10–20% $IgA_2$ while secretory IgA is polymeric and contains 50–75% $IgA_1$ and 25–50% $IgA_2$.

Because of these properties, secretory IgA can bind to the invading organisms more effectively. Therefore, secretory IgA have anti-bacterial, anti-fungal, and anti-viral activities, and play an important role in protection of mucosal surfaces from adherence of microorganisms. This prevention of colonization of the mucous membrane by secretory IgA is done by binding and blocking of specific binding sites on the bacterial cell wall. A decrease in adherence results in enhanced clearance of the bacteria by oral secretion and immunological mechanisms. For this reason in patients with secretory IgA deficiency, frequent infections have been observed.

An additional role of secretory IgA is prevention of diffusion of food antigens into mucous membranes. Therefore, a secretory IgA deficient person is more exposed to high levels of antigens or allergens. This phenomenon, along with T-cell regulatory abnormalities which occurs in most patients with IgA deficiency, make them more prone to development of allergies and autoimmune diseases.

Absence of secretory IgA is the most common immunodeficiency disorder, accounting for 15% of all primary immunodeficiency syndrome cases. Frequency of certain diseases, mainly neurological (24%), gastrointestinal (28%), collagen and autoimmune (20%), and recurrent infections (23%) may occur in patients with selective IgA deficiency. These include neuropathies, endocrinopathies, atopy, celiac disease, asthma, food allergies, rheumatoid arthritis, lupus, malabsorption syndrome, lymphomas, bacterial infections, viral infections, and fungal infections. High levels of total secretory IgA may indicate viral infection or overgrowth of yeast aerobic and anaerobic bacteria in the oral cavity as well as in different parts of the gastrointestinal tract.

This is the basis for a newly developed test called Intestinal Barrier Function (IBF). This test was developed because, in our experience, microbial flora imbalance cannot be fully understood in its diagnostic and therapeutic implications without coordination of all components of the intestinal flora including the dietary antigens. IBF utilizes a highly sensitive and accurate ELISA test method that measures the saliva IgG, IgM, and IgA specific antibody titers to the purified antigens from five different dietary antigens, three aerobic, and two anaerobic microbes, including *Candida albicans, Candida tropicalis* and *Candida cruzei*.

Such quantitative and comparative test results may allow the determination of primary clinical conditions, such as: food allergy or intolerance, intestinal imbalance, gut barrier dysfunction, bacterial translocation, immunodeficiencies, candidiasis, and autoimmunities.

The Intestinal Barrier function test is recommended for patients who have Candidiasis which appears to be resistant to standard therapy; are suspected of suffering from disturbances of intestinal permeability and absorption; complain of food intolerance (including "food allergy"); complain of chemical hypersensitivity, diagnostic problems with multiple symptom complaints (including chronic Fatigue Syndrome); suffer from abnormal immune cell count and function (including autoimmune diseases); or may develop post-operative sepsis due to bacterial translocation.

Laboratory results of patients who may suffer from one or more of the above conditions are presented in the attached figures (FIGS. 3–9).

SUMMARY OF THE INVENTION

One aspect of the present invention is a method for determining a cause for digestive and immune disorders. This method includes the steps of (a) determining a level of antibodies against dietary antigens in a saliva sample from the patient, (b) determining the level of antibodies against normal intestinal microflora in the same or a different sample from the patient, and (c) comparing the levels determined in steps (a) and (b) with normal levels of the same antibodies. Possible outcomes for the comparison include (i) microflora imbalance characterized by higher than normal levels of microflora antigens and normal levels of food antigens, (ii) food allergy or intolerance characterized by higher than normal levels of food antigen antibodies and normal levels of microflora antibodies, (iii) gut barrier dysfunction characterized by higher than normal levels of both food antigen antibodies and microflora antibodies, (iv) immunodeficiency characterized by lower than normal levels of food antigen antibodies and microflora antibodies, and (v) a cause other than indicated in (i) through (iv) characterized by normal levels of both food antigen antibodies and microflora antibodies In one embodiment, an ELISA test is used to determine the levels of antibodies.

In another embodiment, the antigens are chosen from bacteria and yeast.

In another embodiment, the antibodies are IgM, IgG, and IgA.

In a further embodiment, the digestive and immune disorders are food allergy or intolerance, microflora imbalance, gut barrier dysfunction, bacterial traslocation, humoral immunodeficiencies, candidiasis, and autoimmunities.

Further objects, features and other advantages of the present invention become apparent from the ensuing detailed description, considered together with the appended figures.

DETAILED DESCRIPTION OF THE PREFERRED EMBODIMENTS

Figure 1:
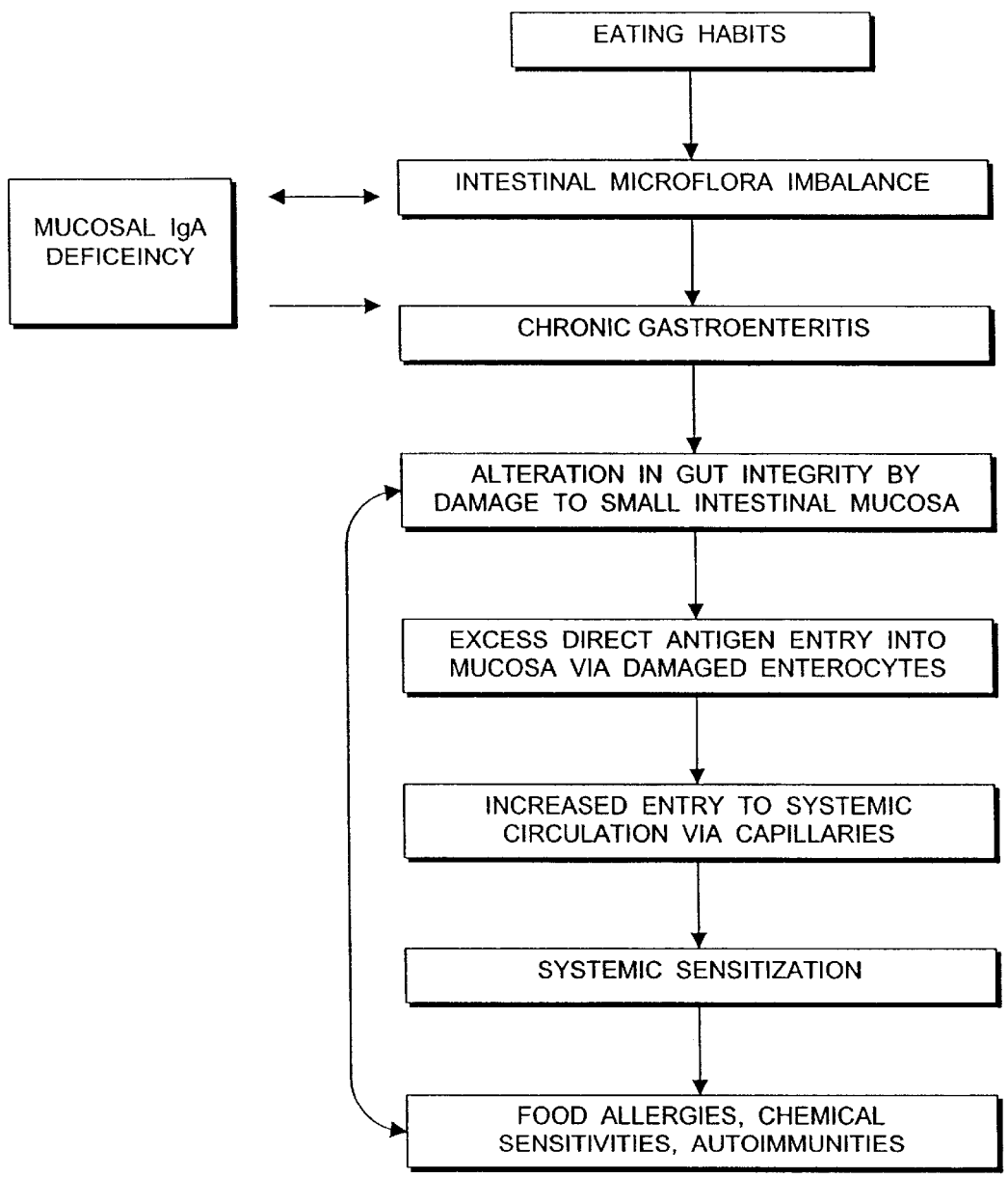
FIG. 1 Excessive uptake of bacterial, fungal, viral and food antigens into the circulation may induce immune response first in the form of IgM and thereafter in the form of IgG and IgA antibodies which results in clinical condition.
Figure 2:
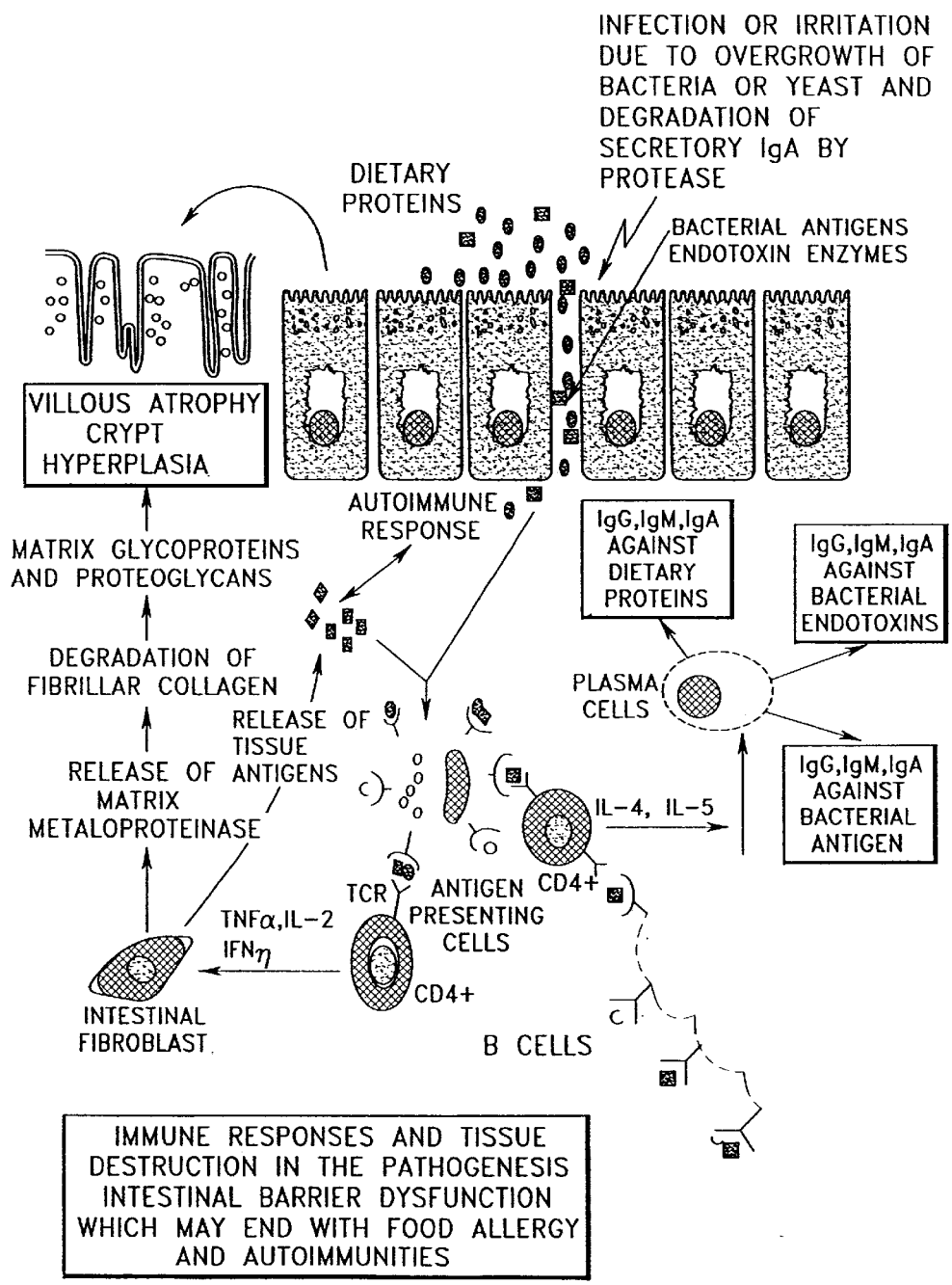
FIG. 2 Immune responses and tissue destruction in the pathogenesis of intestinal barrier dysfunction which may end with food allergy or intolerance and autoimmunities.

We have produced a single test that will accurately inform the physician of important clinical conditions required to diagnose and to treat etiologically patients who may suffer from candidiasis, food allergies, or intolerance, and many other related diseases.

This test was developed since, in our experience, the diseases cannot be fully understood in their diagnostic and therapeutic implications without coordination of the other components of the intestinal flora and dietary antigens.

Conditions that adversely effect the intestinal flora can result in intestinal imbalance and enhanced gut permeability. Such reactions, when coupled with immuno dysfunction, can readily result in food allergies or intolerance, chemical hypersensitivity, candidiasis (candida related complex), some forms of Lupus and rheumatoid arthritis, asthma, chronic migraines, gastrointestinal disorders, as well as cellular immunosuppression.

In order to assist the physician to make a more etiologic based diagnosis, we have developed the Microflora Immune Competency Test (MIT), both in blood and mucosal secretions. Mucosal secretions are secretions of a mucosa, such as saliva. Although saliva is mentioned throughout the disclosure, it is not meant to be limiting and can refer to any mucosal secretion.

MIT utilizes a highly sensitive and accurate ELISA test method that measures the saliva IgG, IgA, and IgM specific antibody titers to the purified antigens from three aerobic (*E. coli,* Lactobacillus, and Enterococcus), two anaerobic microbes (*Bacteroides fragilis* and *Clostridium perfringens*), *Candida albicans,* and dietary antigens.

Such quantitative and comparative test results allow the physician to determine four primary clinical conditions: intestinal imbalance, enhanced gut permeability, humoral immunodeficiencies, and Candidiasis. MIT thus helps the clinical investigator to evaluate and treat patients by using immunological responses as indications of intestinal function and pathology.

MIT is recommended in patients who: have Candidiasis which appears to be resistant to standard therapy; are suspected of suffering from disturbances of intestinal permeability and absorption; have complaints of food intolerance (including "food allergy"); present as diagnostic problems with multiple symptom complaints (including chronic fatigue syndromes); or suffer from abnormal immune cell count and function (including autoimmune diseases).

Although other materials and methods similar or equivalent to those described herein can be used in the practice or testing of the preferred embodiments, the preferred method and materials are now described. Example 1 describes the steps in the Microflora Immune Competency Test.

EXAMPLE 1

The Microflora Immune Competency Test (MIT)

MIT requires only about 1 ml of patient saliva, collected in a sterile tube. Saliva can be stored frozen for up to six months at a laboratory, such as Immunosciences Laboratory, in order to be available for pair testing with samples as necessary to observe the usefulness of treatment.

The purified antigens were immobilized by attachment to a solid surface, such as a microtiter plate. The saliva sample was added to the plate followed by incubation and washing. Antibody bound to antigen was revealed by adding enzyme labeled monoclonal antibody directed against the first immunoglobulin. After addition of substrate, color development was measured by microtiter reader at 405 nm. The intensity of the color was directly related to the concentration of antibodies to these antigens present in patient's saliva.

The matrix of the positive control was human saliva. Because no test method can offer complete assurance that human T-lymphotropic type III/lymphadenopathy associated virus (HTLV-III/LAV), hepatitis B virus or other infectious agents are absent; these reagents were handled at the Biosafety Level 2, as recommended for any potentially infectious human body fluid in the Centers for Disease Control/National Institutes of Health manual "Biosafety in Microbiological and Biomedical Laboratories, 11 1984". All human saliva was found negative for HTLV-III antibody and HbsAG when tested with FDA licensed reagents.

The reagents contained sodium azide as a preservative. Sodium azide may react with lead, copper or brass to form explosive metal azides. To prevent the possible formation of explosive metal azides, all the reagents were disposed of by flushing with large amounts of water through the plumbing system.

Buffers and other kit components were stored at 2–8° C. before and after dilution.

Saliva samples were collected using sterile tubes. A minimum of about 200 µl of saliva was needed for the assay, therefore, about 0.5 ml or more of saliva was recommended. Stored saliva was frozen at −20° C. or lower in tightly sealed sterile tubes. Samples were not repeatedly frozen and thawed and were not stored in self-defrosting freezers because the sample would desiccate and/or immunoglobulin degradation would occur.

Calibrator samples I, II, III as well as positive and negative controls were used.

The wash buffer was made as follows: in a 500 ml graduated cylinder, 450 ml of water was added to 50 ml of 10× wash buffer. The solution was mixed and transferred to a 500 ml squeeze bottle and stored at 2–8° C. until used. Then, 20 ml of conjugate diluent was added to the anti human IgM conjugate and mixed well.

Substrate buffer and Stop Solution were ready for use. (CAUTION: Both solutions are caustic: avoid contact with skin and eyes; rinse with copious amounts of water, in the event of contact.)

The substrate solution was prepared only immediately before use. For 1–5 strips, 5 ml of substrate buffer were pipeted into the empty substrate reconstitution bottle and 1 substrate tablet was dropped in. The bottle was shaken to dissolve the tablet. The buffer was used within an hour after reconstitution as recommended.

Reagent and saliva were prepared as follows. All strips to be used, reagents, controls, and patient's saliva were equilibrated to room temperature (22–25° C.). Patient's saliva was diluted 1:100 with saliva diluent buffer, 20 µl saliva+2.0 ml buffer. Saliva dilutions were made in tubes prior to addition to wells and thoroughly mixed before dispensing. Only one well per test was necessary. For every determination, six strips (1–6) of eight wells were needed to run blank calibrators and four patient's samples.

Well Identification: 6 antigen-coated strips were used. Each was divided into 8 equal-sized squares. The top 6 squares were labeled "BLANK", the next 3 were "CALIBRATOR I, CALIBRATOR II, and CALIBRATOR III".

The last 4 were labeled "SPECIMEN I, SPECIMEN II, SPECIMEN III and SPECIMEN IV". Note: Blank and calibrators may need to be positioned differently if specified by the instrument manufacturer. For each test performance the following wells were used: One blank well (reagent blank), one well each for Calibrator I, II and III, and one well each for patient specimens.

The assay procedure was as follows: 100 µl of saliva diluent buffer was pipeted into all eight wells of strip #1, 2, 3, 4, 5, and 6. The contents were discarded and the addition of saliva diluent buffer to the same wells was repeated. Then, 100 µl of each calibrator or patient saliva dilutions were pipetted into identified wells; being careful to avoid splashing and air bubbles because cross-contamination between the wells may cause erroneous results. Then, 100 µl of saliva diluent buffer was pipeted into a blank well. The reagents were dispensed slowly to avoid splashing and air bubbles. If large air bubbles occurred, they were aspirated or the plate was gently shaken. The plate was covered and incubated for 60 minutes at room temperature (22–25° C.). Saliva was shaken from the wells into a container containing disinfectant solution or aspirated with a vacuum device. All wells were empty prior to filling with 1× wash buffer and allowing a 10–20 second soak time. The wells were emptied by shaking into a disposal container or aspirated. Washing was repeated three more times. The inverted plate was tapped onto a paper towel to completely remove all residual liquid. Then, 100 µ; of anti IgA, IgG, or IgM conjugate was added to the tested strips. The plate was covered and incubated for 60 minutes at room temperature (22–25° C.). The liquid was shaken or aspirated from all the wells and washed four times. Then, 100 µl of p-NPP substrate was added to all the wells at timed intervals which corresponded to the reading time of the instrument used to read the reactions. The 45-minute incubation time was started as substrate was added to the first well. The plate was covered and incubated 45 minutes at 22–25° C. (The assay may be incubated for less than 45 minutes if incubation temperature is higher than 25° C.). Then, 50 µl of 3N NaOH was pipeted into all the wells at the same timed intervals that the p-NPP was added. The plate was shaken for 1–2 minutes by hand or on a shaker, avoiding splashing. The bottom of the wells was wiped with a non-abrasive paper towel and the instrument was zeroed on the blank well. The OD was read at 405±5 nm within 30-minutes, and reactions recorded.

The ELISA values for the calibrators used in this test system were as follows: Calibrator I=400, Calibrator II=3, 200, Calibrator III=12,800.

ELISA values for each test specimen were determined using the following formula:

$$\text{ELISA values of test specimen} = \frac{\text{Values of calibrator} \times \text{Absorbance of test specimen}}{\text{Absorbance of calibrator}^*}$$

*Out of three calibrator values, the absorbance of the one which is closest to the absorbance of the test specimen was used for the calculations. Examples of how calibrations were performed for each Organism are shown using Test Specimen 1 in the following calculations.

Test Specimen 1: IgA Calculation for Organism 1 (Candida)
ELISA Values of Calibrator III—12800
Absorbance of Calibrator 111=1.96
Absorbance of test specimen=1.28
IgA ELISA values of test specimen?

$$\text{IgA ELISA values of test specimen} = \frac{12800 \times 1.28}{1.96} = 8359$$

Test Specimen 1: IgA Calculation for Organism II (Aerobic)
ELISA values of Calibrator II=3200
Absorbance of Calibrator II=0.561
Absorbance of test specimen=0.632
IgA ELISA values of test specimen?

$$\text{IgA ELISA values of test specimen} = \frac{3200 \times 0.632}{0.561} = 2253$$

Test Specimen 1: IgA Calculation for Organism III (Aerobic)
ELISA values of Calibrator II=3200
Absorbance of Calibrator 11=0.456
Absorbance of test specimen=0.214
IgA ELISA Values of test specimen?

$$\text{IgA ELISA values of test specimen} = \frac{3200 \times 0.314}{0.456} = 938$$

Test Specimen 1: IgA Calculation for Organism IV (Aerobic)
ELISA values of Calibrator II=3200
Absorbance of Calibrator II=0.545
Absorbance of test specimen=0.621
IgA ELISA values of test specimen?

$$\text{IgA ELISA values of test specimen} = \frac{3200 \times 0.621}{0.545} = 2278$$

Test Specimen 1: IgA Calculation for Organism V (Anaerobic)
ELISA values of Calibrator III=12800
Absorbance of Calibrator III=1.72
Absorbance of test specimen=1.68
IgA ELISA values of test specimen?

$$\text{IgA ELISA values of test specimen} = \frac{12800 \times 1.68}{1.73} = 12502$$

Test Specimen 1: IgA Calculation for organism VI (Anaerobic)
ELISA values of Calibrator III=12800
Absorbance of Calibrator III=1.58
Absorbance of test specimen=1.79
IgA ELISA values of test specimen?

$$\text{IgA ELISA values of test specimen} = \frac{12800 \times 1.79}{1.58} = 14501$$

CONCLUSION: Intestinal flora imbalance is evidenced by high ELISA values for candida and anaerobic bacteria. For more information and better interpretation of test results, use Table 1.

TABLE 1

DATA INTERPRETATION
IgA ANTIBODY LEVELS TO DIFFERENT
ANTIGENS OF GI TRACT IN SALIVA

| DIETARY PROTEIN | YEAST | AEROBIC BACTERIA | ANAEROBIC BACTERIA |
|---|---|---|---|
| HIGH | HIGH | HIGH | HIGH |
| Simultaneous increase in IgA, IgG, or IgM titers against all the above microorganisms is indicative of enhanced gut mucosa permeability. | | | |
| HIGH | NORMAL | NORMAL | NORMAL |
| High IgA, IgG, or IgM against dietary proteins indicate food allergy or intolerance. | | | |
| NORMAL | HIGH | NORMAL | NORMAL |
| High IgA, IgG, or IgM titers against Candida may be an indication of Candida overgrowth due to intestinal imbalance. | | | |
| NORMAL | NORMAL | HIGH | HIGH |
| High IgA, IgG, or IgM titers against aerobic and anaerobic bacteria may be an indication of bacterial overgrowth due to intestinal imbalance. | | | |
| LOW | LOW | LOW | LOW |
| Very low titers of IgA, IgG, or IgM against all the above dietary proteins and microorganisms are an indication of mucosal and humoral immunodeficiency. | | | |
| NORMAL | NORMAL | NORMAL | NORMAL |
| Normal titers of IgA, IgG, or IgM antibodies against the above antigens are an indication of balanced mucosal immunity and intestinal microflora. | | | |

For precise determination, absorbances were converted to ELISA values using a point-to-point data reduction method. (However, one may substitute a best-fit linear regression program to obtain values). If a program is used to provide calculation of ELISA values, the calibrator ELISA values (which appear on vial label) should be entered as the "standards".

The values were obtained manually and plotted using linear graph paper. The X-axis was each calibrator's ELISA value. The Y-axis was the corresponding mean absorbance value. A line was drawn to connect the three points. The ELISA value of each patient's saliva was obtained by locating its absorbance on the Y-axis and finding the corresponding ELISA value on the X-axis.

For test validation, calibrators and control saliva were run with each test run and the following qualities were observed.

a) The conjugate blank must had an absorbance lower than that of the negative.

b) The mean absorbance of Calibrator I (negative) was lower than that of Calibrator II (low positive) and <0.500.

c) The mean absorbance of Calibrator III (high positive) was higher than the mean absorbance of Calibrator II, but not exceed 2.5A.

d) The test was found to be valid when controls, positive and negative, both fell within reasonable ELISA value ranges.

EXAMPLE 2

Measurement of Saliva Secretory IgA

The secretory IgA binding molecules, such as anti-secretory component, are immobilized by attachment to a solid surface, such as a microtiter plate. The saliva sample is added to the plate followed by incubation and washing. Secretory IgA bound to the plate is revealed by adding enzyme labeled monoclonal antibody directed against human IgA. Finally, after the addition of substrate, color development is measured by a microtiter reader at 405 nm. The intensity of the color is directly related to the concentration of secretory IgA present in the patient's saliva.

Experimental conditions are similar to Example 1. Saliva samples were collected in sterile tubes.

Well Identification: Antigen-coated strips were used. Each was divided into 8 equal-sized squares. The top square was labeled "BLANK", the next 4 were "CALIBRATOR I, CALIBRATOR II, CALIBRATOR III, and CALIBRATOR IV". Two wells are for negative antibody and two wells are for positive antibody. The last 3 were labeled "SPECIMEN I, SPECIMEN II, and SPECIMEN III".

The assay procedure was as follows: 100 $\mu$l of saliva diluent buffer was pipeted into all wells. Then, 100 $\mu$l of each calibrator or patient saliva dilutions were pipeted into identified wells; being careful to avoid splashing and air bubbles because cross-contamination between the wells may cause erroneous results. Then, 100 $\mu$l of saliva diluent buffer was pipeted into the blank well. The reagents were dispensed slowly to avoid splashing and air bubbles. If large air bubbles occurred, they were aspirated or the plate was gently shaken. The plate was covered and incubated for 60 minutes at room temperature (22–25° C.). Saliva was shaken from the wells into a container containing disinfectant solution or aspirated with a vacuum device. All wells were empty prior to filling with 1×wash buffer and allowing a 10–20 second soak time. The wells were emptied by shaking into a disposal container or aspirated. Washing was repeated three more times. The inverted plate was tapped onto a paper towel to completely remove all residual liquid. Then, 100 $\mu$l of anti IgA conjugate was added to the tested strips. The plate was covered and incubated for 60 minutes at room temperature (22–25° C.). The liquid was shaken or aspirated from all the wells and washed four times. Then, 100 $\mu$l of p-NPP substrate was added to all the wells at timed intervals that corresponded to the reading time of the instrument used to read the reactions. The 45-minute incubation time was started as substrate was added to the first well. The plate was covered and incubated 45 minutes at 22–25° C. (The assay may be incubated for less than 45 minutes if incubation temperature is higher than 25° C.). Then, 50 $\mu$l of 3N NaOH was pipeted into all the wells at the same timed intervals that the p-NPP was added. The plate was shaken for 1–2 minutes by hand or on a shaker, avoiding splashing. The bottom of the wells was wiped with a non-abrasive paper towel and the instrument was zeroed on the blank well. The OD was read at 405±5 nm within 30-minutes, and reactions recorded.

The ELISA values for the calibrators used in this test system were as follows: Calibrator I=5, Calibrator II=15, Calibrator III=50.

ELISA values for each test specimen were determined using the following formula, as shown in Example 1:

$$\text{ELISA values of test specimen} = \frac{\text{Values of calibrator} \times \text{Absorbance of test specimen}}{\text{Absorbance of calibrator}}$$

EXAMPLE 3

Test for Dietary Antigens

Figure 3:
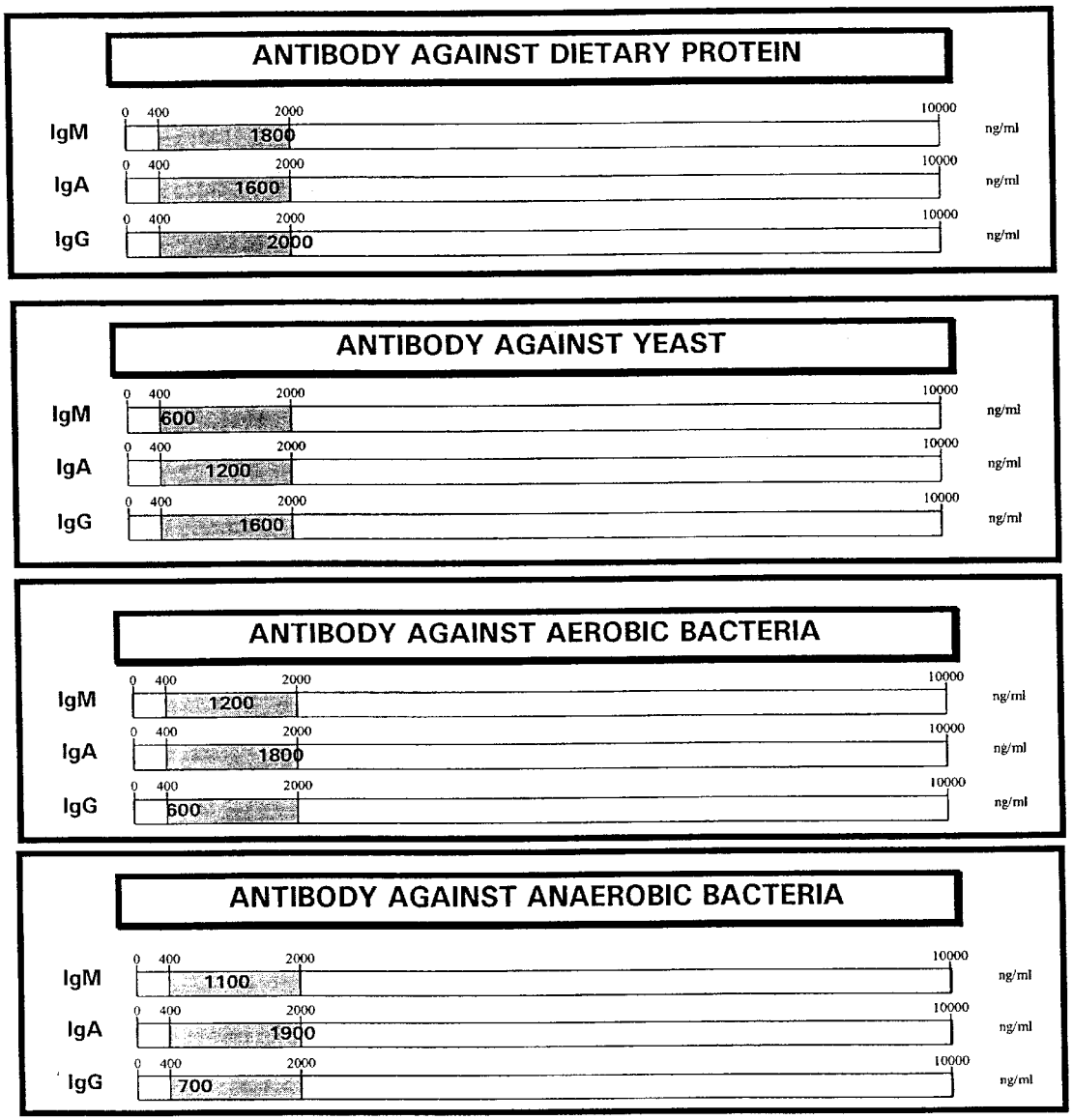
FIG. 3 Example of the test profile for a normal control patient.
Figure 5:
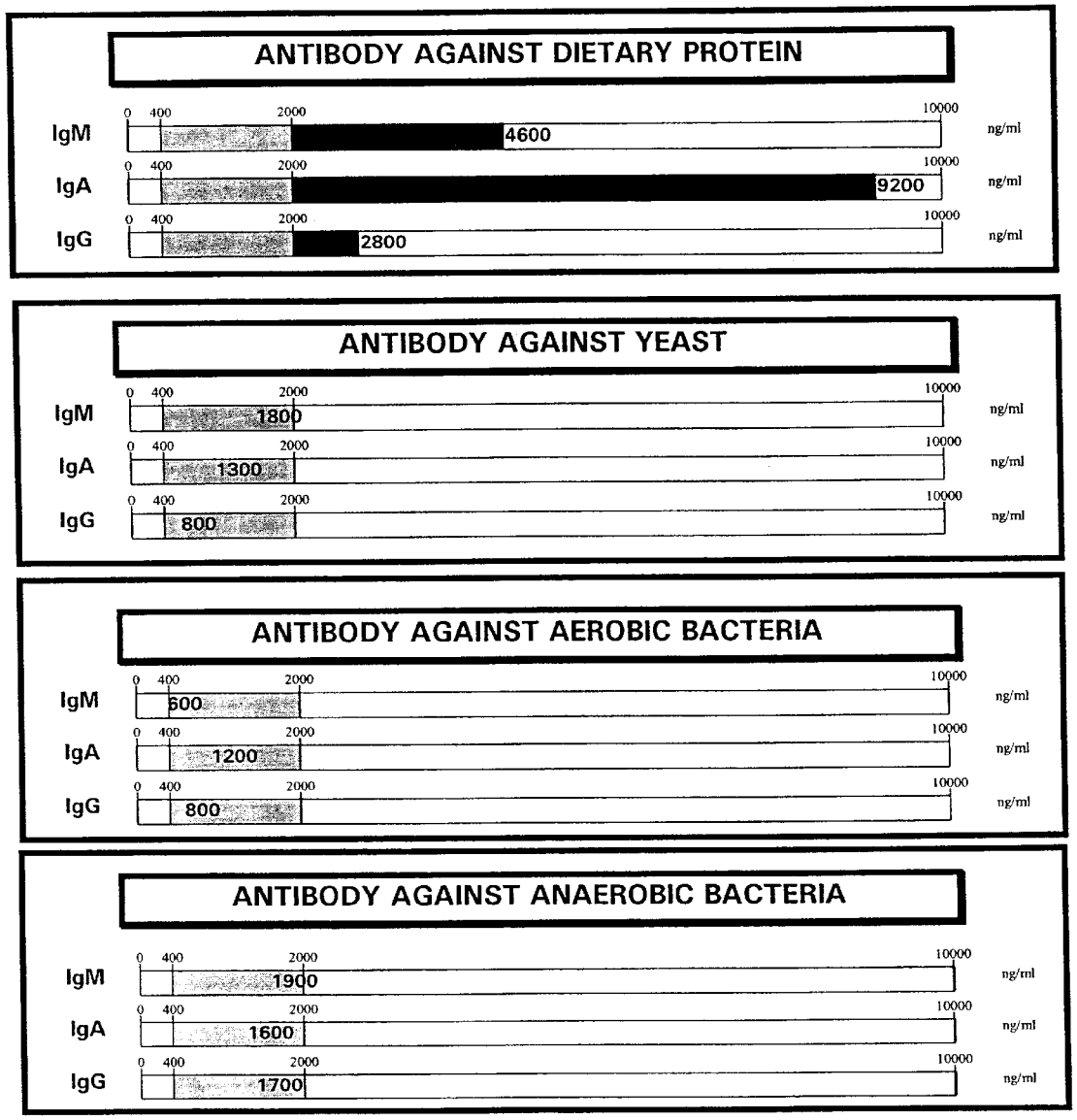
FIG. 5 Example of the test profile for a patient showing food allergy or intolerance.
Figure 9:
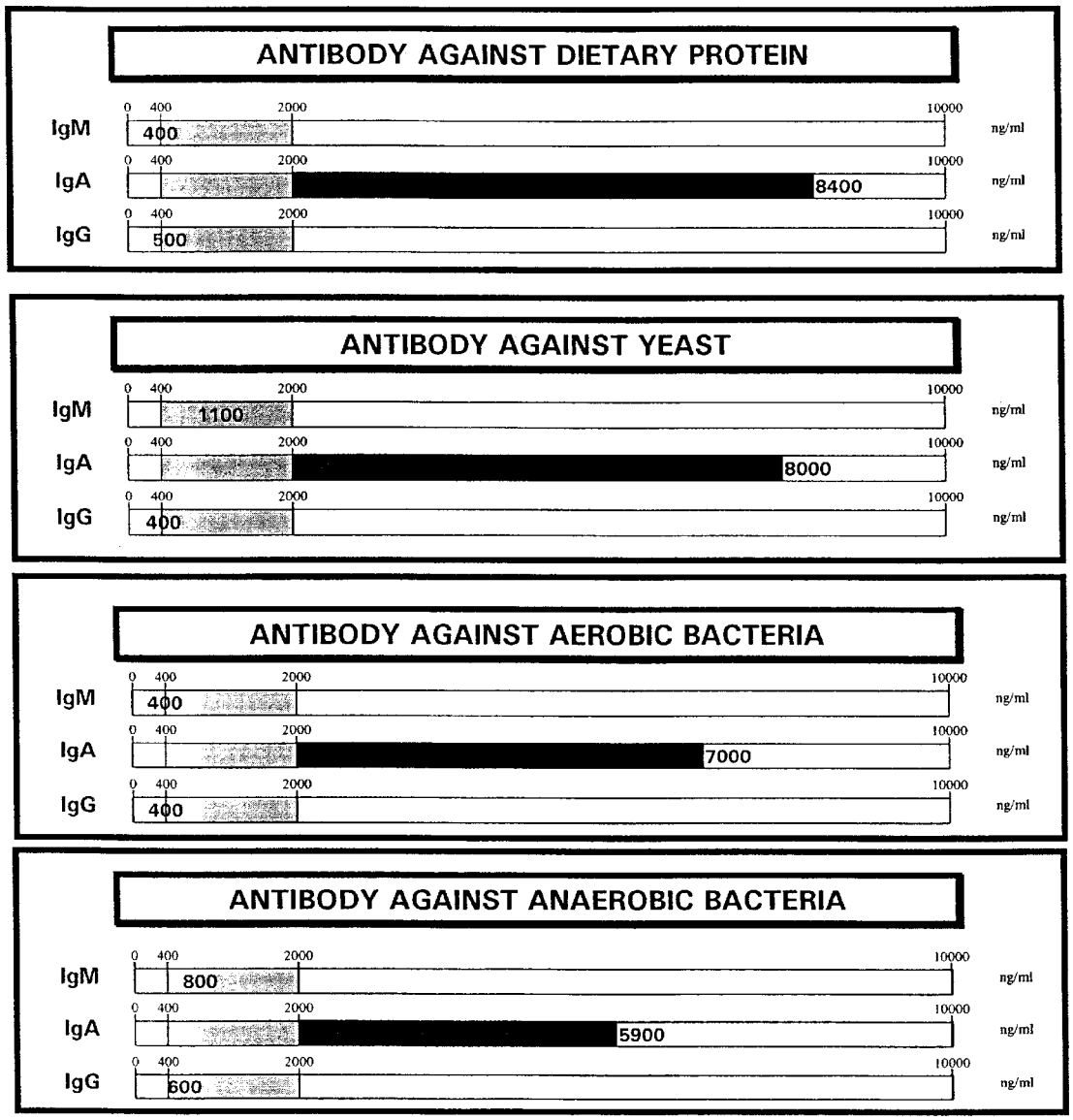
FIG. 9 Example of the test profile for a patent showing gut barrier dysfunction or enhanced permeability to high molecular weight antigens.

To test for levels of antibodies to dietary antigens, the tests in Example 3 are performed using antigens consisting of dietary antigens which are immobilized by attachment to a solid surface, such as a microtiter plate. The dietary antigens can be chosen from wheat proteins, soy, corn, milk, egg, and meat. Normal levels of antibodies to these proteins are shown in FIG. 3 and are typically 400–2000 ELISA units. High levels (greater than 2000 ELISA units) of one or all types of immunoglobulins, IgA, IgM, and IgG to dietary antigens is diagnostic of a food allergy or intolerance, as seen in FIG. 5. If high levels of IgM to dietary antigens is seen in conjunction with high levels to microflora antigens, it is diagnostic of a gut barrier dysfunction, as seen in FIG. 9.

EXAMPLE 4

Analysis of Results

Results were analyzed as a panel. The values for aerobic bacteria, anaerobic bacteria, and yeast represent the values for any normal intestinal microflora that are tested. In this case the yeast were selected from Candida species, including *C. albicans, C. tropicalis,* and *C. cruzei.* The aerobic bacteria used were *Escherichia coli,* Lactobacillus species, and Enterococcus species. The anaerobic bacteria used were *Bacteroides fragilis,* and *C. perfringens.* The dietary antigens were selected from wheat, soy, corn, milk, egg, and meat. Secondary antibodies to IgG, IgM, and IgA were used to look for specific subsets of immunoglobulins.

In FIG. 3 the test profile for a normal control patient is shown. Levels of all types of immunoglobulins were tested. Normal antibody levels to the chosen antigens typically range between 400 and 2000 ELISA units.

Figure 4:
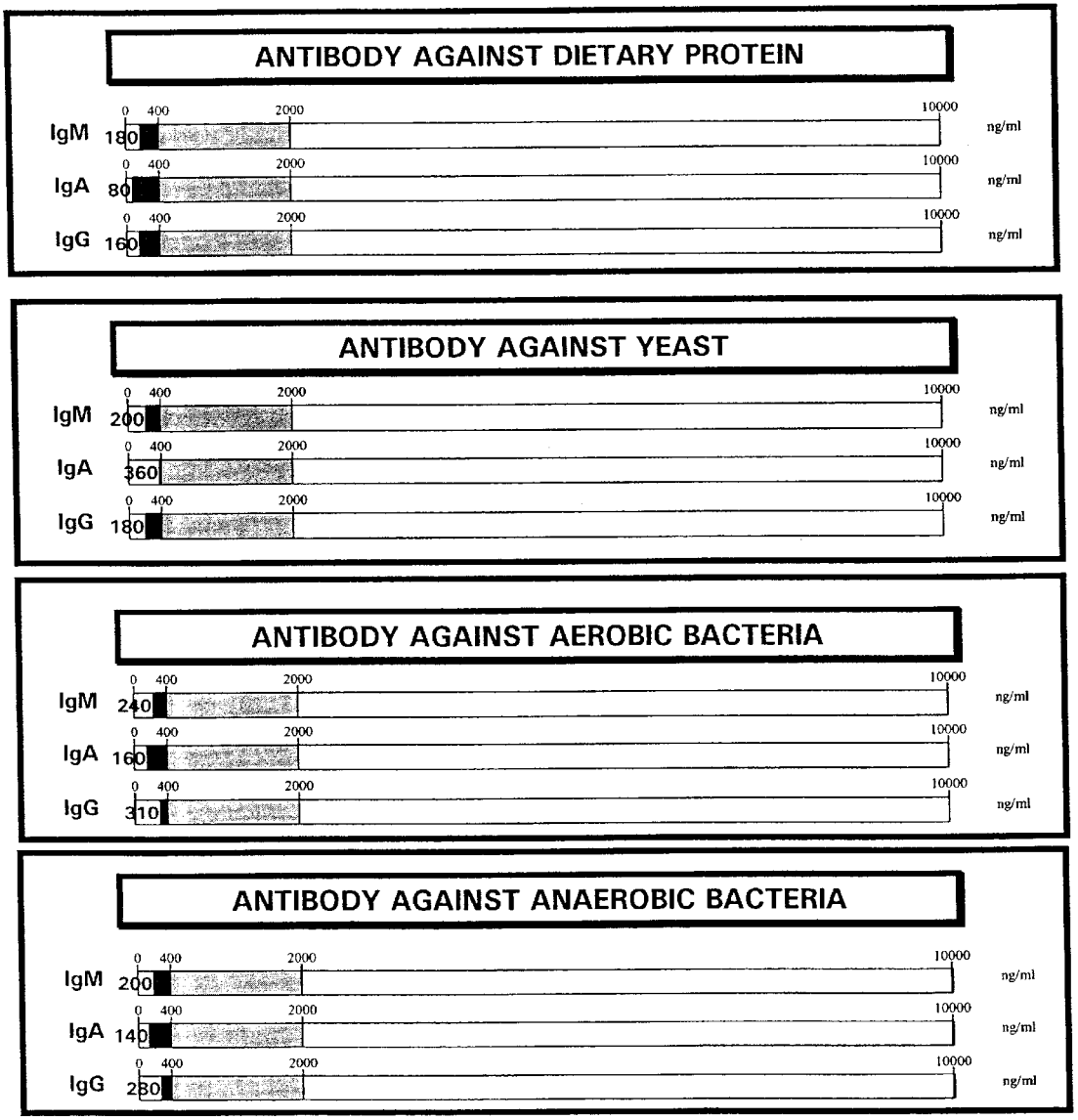
FIG. 4 Example of the test profile for a patient showing humoral immunodeficiency.

FIG. 4 shows a profile for a patient who is immunodeficient. The antibody levels in the patient's saliva to all antigens were less than normal. Typical values were less than 400 ELISA units.

FIG. 5 shows the test profile for a patient with a food allergy or intolerance. The patient had increased antibody levels to dietary antigens far above normal and, in this case 2800 to 9200 ELISA units. However, the antibody levels to intestinal microflora were in the normal range.

Figure 6:
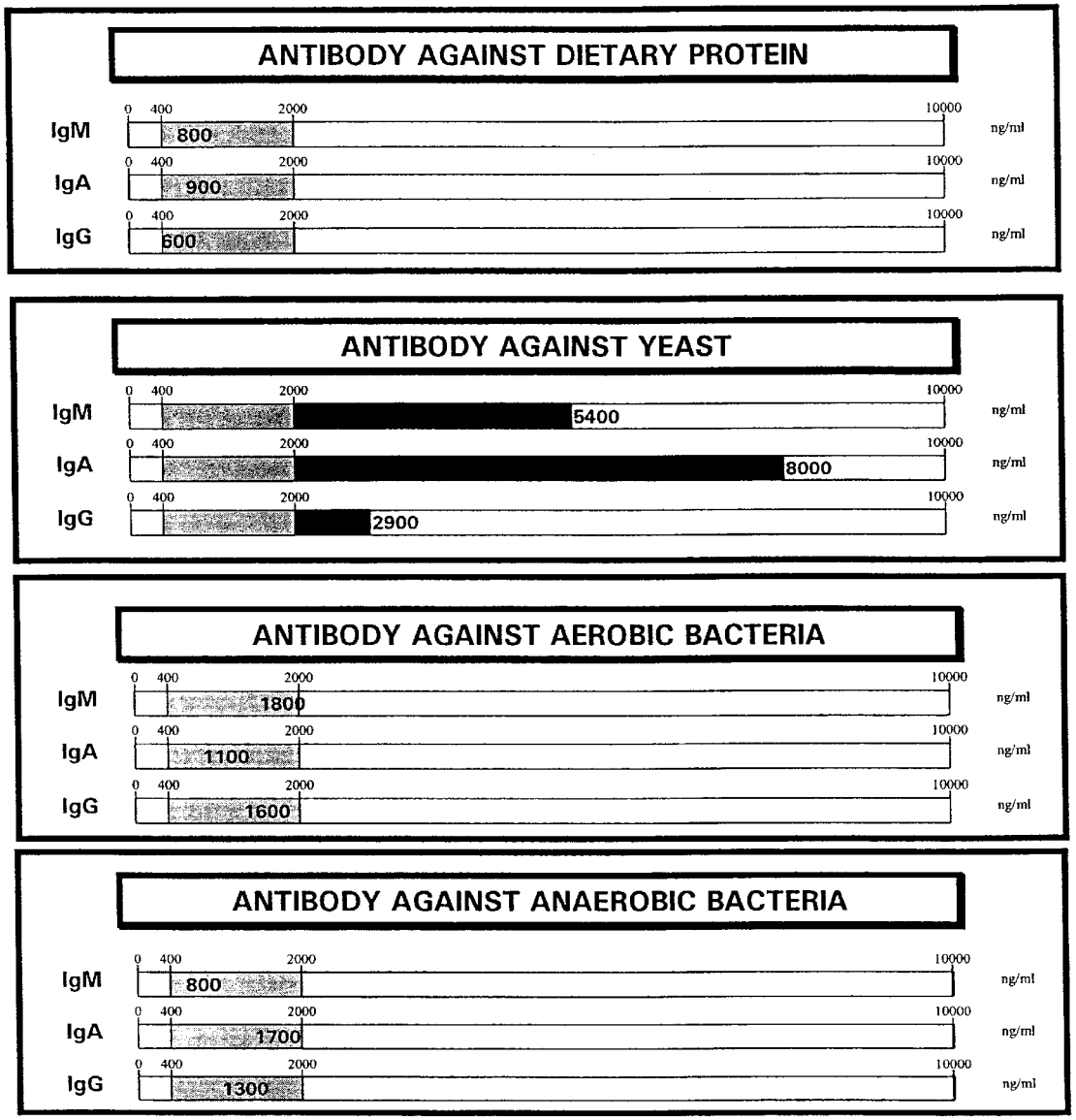
FIG. 6 Example of the test profile for a patient showing yeast overgrowth.

A patient with a yeast overgrowth showed the test profile in FIG. 6. Levels of all antibody types to yeast antigens were higher than normal, in this case from 2900 to 8000 ELISA units. Levels of antibodies to dietary antigens, and other microflora were normal.

Figure 7:
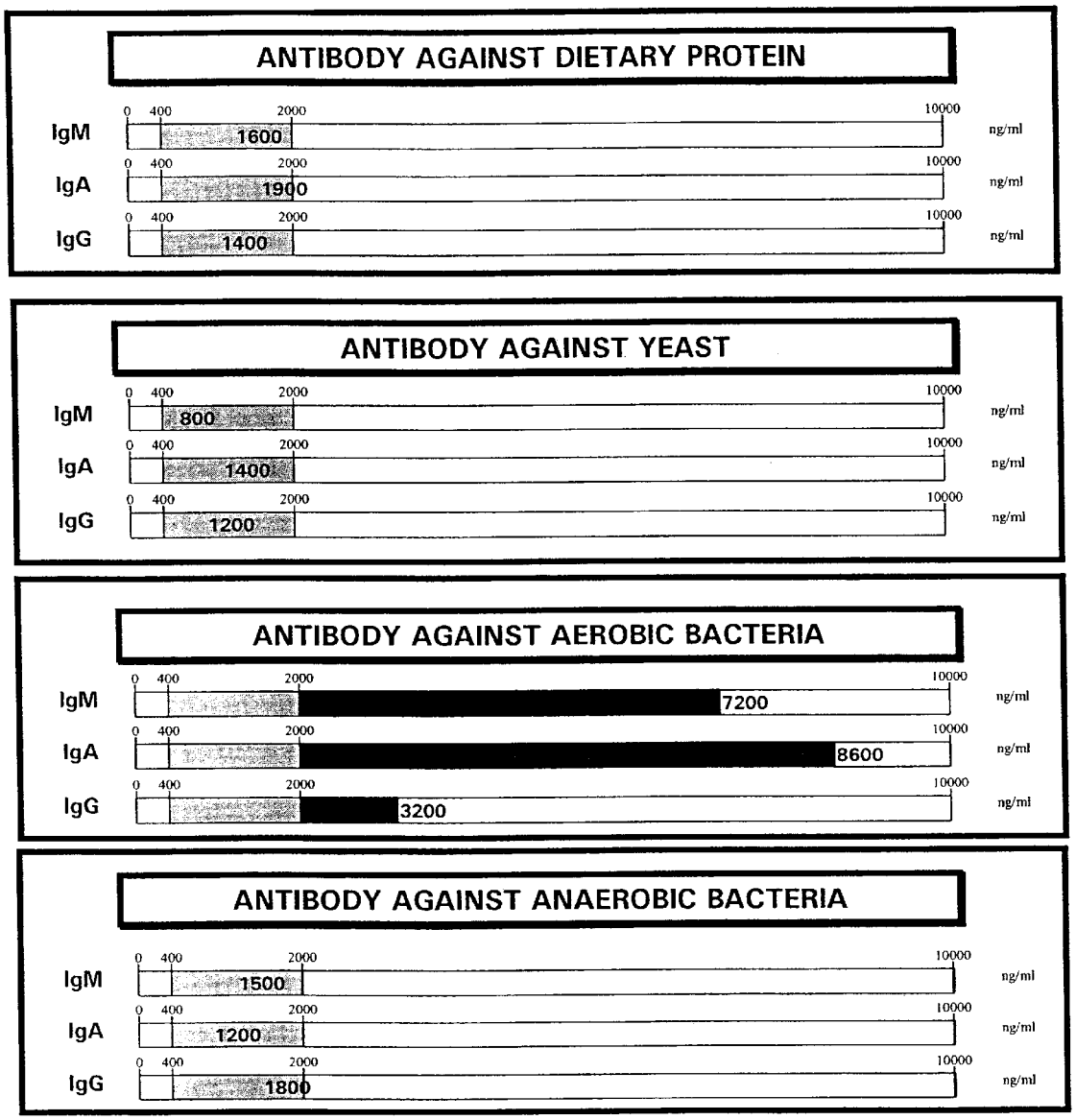
FIG. 7 Example of the test profile for a patient showing microflora imbalance of aerobic bacteria.

In FIG. 7, a patient with one type of microflora imbalance is shown. This patient had elevated levels of antibodies to aerobic bacteria, from 3200 to 8600 ELISA units, while antibodies to other microflora and dietary antigens was normal. Therefore, this patient had an overgrowth of aerobic microflora.

Figure 8:
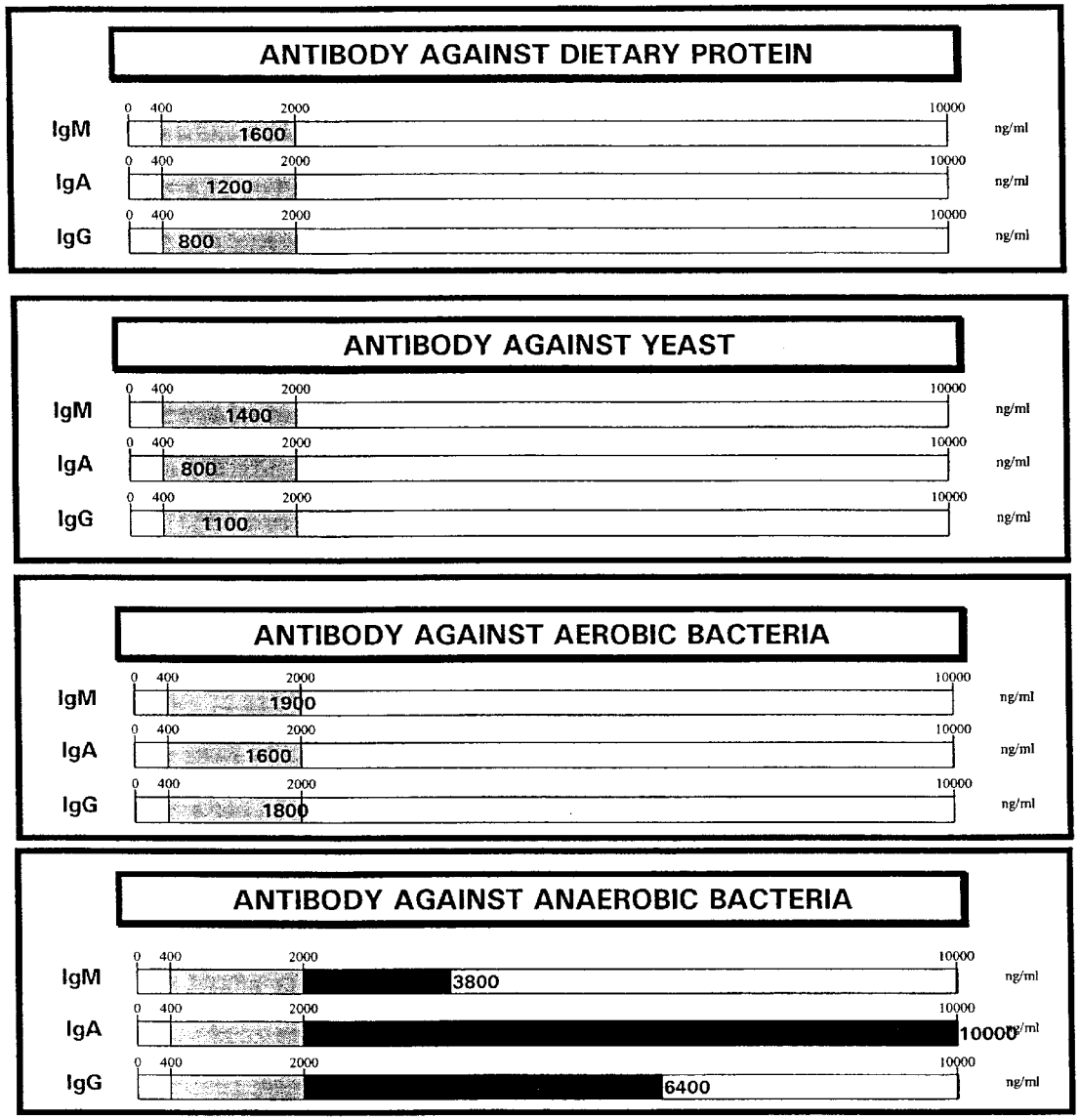
FIG. 8 Example of the test profile for a patient showing microflora imbalance of anaerobic bacteria.

In FIG. 8, a patient with another type of microflora imbalance is shown. This patient had elevated levels of antibodies to anaerobic bacteria, from 3800 to 10,000 ELISA units, while antibodies to other microflora and dietary antigens was normal. Therefore, this patient had an overgrowth of anaerobic microflora.

A patient with a gut barrier dysfunction showed the test profile in FIG. 9. Levels of IgA to all antigens tested were higher than normal, in this case from 5900 to 8400 ELISA units. Levels of other types of antibodies were normal. This is because IgA is produced against recent entrance of antigens into the circulation and other antibodies may follow thereafter.

There is a correlation between low or high secretory IgA in saliva with the levels of IgA antibodies against dietary proteins, yeast, aerobic bacteria, and anaerobic bacteria in saliva. The normal ranges are taken from tests of about 500 healthy individuals. These correlations are shown in the tables below.

I. CORRELATION BETWEEN LOW SECRETORY IGA IN SALIVA WITH THE LEVELS OF IGA ANTIBODIES Against Dietary Proteins, Yeast, Aerobic and Anaerobic Bacteria in Saliva

| Saliva Sample Number | Secretory IgA IgA Antibody Normal Range 10–28 units | Dietary Proteins IgA Antibody Normal Range 400–2000 units | Yeast IgA Antibody Normal Range 400–2000 units | Aerobic Bacteria IgA Antibody Normal Range 400–2000 units | Anaerobic Bacteria IgA Antibody Normal Range 400–2000 units |
|---|---|---|---|---|---|
| 1 | 4.0 | 200 | 260 | 180 | 210 |
| 2 | 1.0 | 100 | 120 | 100 | 80 |
| 3 | 6.0 | 160 | 140 | 210 | 200 |
| 4 | 5.0 | 200 | 180 | 120 | 100 |
| 5 | 3.0 | 240 | 120 | 160 | 200 |
| 6 | 2.0 | 100 | 130 | 180 | 260 |
| 7 | 6.0 | 210 | 280 | 290 | 310 |
| 8 | 4.0 | 320 | 300 | 310 | 270 |
| 9 | 5.0 | 400 | 280 | 390 | 600 |
| 10 | 7.0 | 310 | 360 | 400 | 410 |
| 11 | 6.0 | 600 | 800 | 540 | 480 |
| 12 | 10.0 | 800 | 2,200 | 1,200 | 800 |
| 13 | 2.0 | 160 | 210 | 320 | 390 |
| 14 | 3.0 | 80 | 370 | 210 | 180 |
| 15 | 1.0 | 120 | 140 | 260 | 400 |

Low levels of secretory IgA (<10 units) in saliva correlate with very low levels of IgA antibodies against one or a combination of dietary proteins, yeast, aerobic bacteria, and anaerobic bacteria. A low total level of secretory IgA indicates mucosal immune deficiency and a lack of immune reaction of the cells involved in mucosal immunity to a variety of antigens (dietary, yeast, aerobic bacteria, anaerobic bacteria and others) that the gut mucosa is exposed to. In patients with low secretory IgA, simultaneous blood and saliva testing should be performed against dietary proteins, yeast, aerobic bacteria, and anaerobic bacteria in order to confirm whether or not the patient is suffering from mucosal immune deficiency, humoral immune deficiency, or both.

II. CORRELATION BETWEEN HIGH SECRETORY IGA IN SALIVA WITH
THE LEVELS OF IGA ANTIBODIES
Against Dietary Proteins, Yeast, Aerobic and Anaerobic Bacteria in Saliva

| Saliva Sample Number | Secretory IgA IgA Antibody Normal Range 10–28 units | Dietary Proteins IgA Antibody Normal Range 400–2000 units | Yeast IgA Antibody Normal Range 400–2000 units | Aerobic Bacteria IgA Antibody Normal Range 400–2000 units | Anaerobic Bacteria IgA Antibody Normal Range 400–2000 units |
|---|---|---|---|---|---|
| 1 | 38 | 6,300 | 9,200 | 8,300 | 5,900 |
| 2 | 30 | 4,400 | 8,500 | 2,600 | 3,300 |
| 3 | 29 | 2,400 | 6,700 | 1,400 | 1,300 |
| 4 | 60 | 8,900 | 8,000 | 7,000 | 7,600 |
| 5 | 47 | 2,500 | 9,400 | 1,500 | 3,000 |
| 6 | 41 | 1,600 | 9,600 | 5,700 | 2,600 |
| 7 | 73 | 8,400 | 6,900 | 9,900 | 8,100 |
| 8 | 39 | 4,100 | 3,800 | 6,300 | 3,400 |
| 9 | 35 | 6,800 | 4,700 | 2,000 | 3,800 |
| 10 | 43 | 2,900 | 3,900 | 2,400 | 4,300 |
| 11 | 58 | 6,700 | 2,400 | 3,300 | 9,800 |
| 12 | 32 | 4,500 | 3,600 | 2,900 | 1,600 |
| 13 | 39 | 6,100 | 4,200 | 1,800 | 3,700 |
| 14 | 30 | 2,400 | 2,700 | 1,200 | 3,100 |
| 15 | 64 | 10,600 | 9,500 | 11,600 | 8,300 |

High levels of secretory IgA (>28 units) in saliva correlate with high levels of IgA antibodies against one or a combination of dietary proteins, yeast, aerobic bacteria, and anaerobic bacteria. A high total level of secretory IgA indicates the exposure of cells involved in mucosal immunity to a significant level of antigens which originate, either from dietary proteins or from infectious agents such as yeast, aerobic bacteria, and anaerobic bacteria which are part of microflora of the oral cavity and the gut. However, other infectious agents, including bacteria, virus, or parasites may induce a similar induction of secretory IgA elevation.

The results of the test panels shown in combination with other clinical data and evaluation by the clinician allows for a faster and more accurate diagnosis of the above indications.

REFERENCES

1. Tancrede, C: Role of human microflora in health and disease. Eur J Clin Microbiol Infect Dis 11:1012–5,1992.
2. Bengmark, S: Econutrition and health maintenance—a new concept to prevent GI inflammation, ulceration, and sepsis. Clin Nutr 15:1–10, 1996.
3. Bengmark, S; Gianotti, L: Nutritional support to prevent and treat multiple organ failure. World J Surg 20:474–81, 1996.
4. Bengmark, S: Ecological control of the gastrointestinal tract. The role of probiotic flora. GUT 42:2–7, 1998.
5. Crotty, B: Ulcerative colitis and xenobiotic metabolism. Lancet 343:35–38, 1994.
6. Gruskay, F L; Cooke, R E: The gastrointestinal absorption of unaltered protein in normal infants and in infants recovering from diarrhoea. Pediatrics 16:763–768, 1955.
7. Scadding, G K; Brostoff, J: Immunological response to food. In Food and the gut, Chapter 7, pp. 94–112. Edited by J. O. Hunter and V. Alan Jones. Published by W. B. Saunders, 1985; Sussex, England.
8. Walker, W A: Mechanisms of antigen handling by the gut in clinics. In Immunology and Allergy, Chapter 2, pp-1540. Edited by I. Ballieux R E; Brosto F F J; Fahey J E; Fauci A; Reeves W G; Seligmann M; Thompson R A; and R. Wright. Published by W B Saunders, 1985; Sussex, England.
9. Donaldson, R M: Normal Bacterial Formations of the Intestine and Their Relation to Intestinal Function. New England J of Medicine 270:994–999, 1964.
10. Strombeck, DR; Harviold, D: Binding of cholera toxin to mucin and inhibition by gastric mucin. Infection and Immunity1:1266,1272,1974.
11. Kraft, S C; Rothbert, R M; Kramer, C M: Gastric output and circulating anti-BSA in adults. Clin and Exp Immunol 2:321–326, 1967.
12. Dack, G M; Petran, E: Bacterial activity in different levels of intestine and in isolated segments of small and large bowel in monkeys and dogs. J of Inf Dis 54:204–107,1934.
13. Triger, D R; Cynamon, M H; Wright, R: Studies on hepatic uptake of antigen. Comparison of inferior vena cava and portal vein routes of immunization. Immunology 25:941–950,1973.
14. Straus, W: Use of horseradish peroxidase as a marker protein for studies of phagolysosomes, permeability and immunology. Methods and Achievements in Experimental Pathology 4:54–91, 1969.
15. Jacques, P J: Endocytosis in lysosomes. Biology and Pathology, Chapter 13, pp. 395–420. Dingle, J T; Fell, H B. North Holland Publishing, 1969; Amsterdam.
16. Weissman, G; Dukor: The role of lysosomes in immune responses. Adv in Immuno 112:283–330,1970.
17. Petty, R E; Palmer, N R; Cassidy, J J: The association of autoimmune disease and anti-IgA antibodies in patients with selective IgA deficiency. Clin and Exp Immuno 37:83–88, 1979.
18. Walker, W A; Isselbacher, K J: Intestinal antibodies. New Engl J of Med 297:767773, 1977.
19. Zinneman, H H; Kaplan, A P: The association of girardiasis with reduced intestinal secretory immunoglobulin. Digestive Diseases 17:793–797, 1972.
20. Phillip, A; Mackowiak, M D: The normal microbial flora, medical progress section. New EngJqfMed307:83–93,1982.

21. Jackson, P G; Baker, R W; Lessof, M H; Ferret; J; MacDonald, D M: Intestinal permeability in patients with eczema and food allergy. Lancet 1:1285–1286, 1981.
22. Marshall, J C; Christou, N V. et al: Immunomodulation by altered gastrointestinal tract flora. Arch Surg 123:1465–1469, 1988.
23. Deitch, E A; Xu, D. et al: Bacterial translocation from the gut impairs systemic immunity. Surgery 109:269–276.
24. Fubura, E S; Freter, R: Protection against enteric bacterial infection by IgA. J of Immunol 111:395–399, 1973.
25. Sanderson, I R; Walker, W A: Uptake and transport of macromolecules by the intestine: possible role in clinical disorders (an update). Gastroenterology 104:622–39, 1993.
26. Dupont, C; Barau, E; Molkhou, P; Raynaud, F; Barbet, J P; Dehennin, L: Food induced alterations of intestinal permeability in children with cow's milk-sensitive enteropathy and atopic dermatitis. JPed Gastroentero Nutr 8:459–65, 1989.
27. Jalonen, T: Identical intestinal permeability change children with different clinical manifestations of cow's milk allergy. J All Clin Immunol 88:737–42,1991.
28. Heyman, M; Grasset, E; Ducroc, R; Desjeux, J F: At absorption by the jejunal epithelium of children with mild allergy. Pediatr Res 24:197–202, 1988.
29. Majaxnaa, H; Isolauri, E: Evaluation of the gut mucosal barrier: evidence for increased antigen transfer in children with atopic eczema. J All Clin Immunol 97:985–990, 1996.
30. Lunn, P G; Northrop, C A; Northrop, A J: Automated enzymatic assays for the determination of intestinal permeability probes in urine. 2-mannitol. Clinica Chimica Acta 183:163–170, 1989.

What is claimed is:

1. A method for determining the presence of digestive disorders in a patient, comprising:
   (a) determining a level of antibodies against a dietary antigen in a first sample of a mucosal secretion from said patient;
   (b) determining a level of antibodies against a microorganism found in normal intestinal microflora in a second sample of a mucosal secretion from said patient, wherein first and second samples are the same or different,
   (c) comparing the levels determined in steps (a) and (b) with normal levels of said antibodies, wherein
      (i) higher than normal levels of intestinal micro flora antibodies and normal levels of dietary antigen antibodies indicate an intestinal micro flora imbalance,
      (ii) higher than normal levels of dietary antigen antibodies and normal levels of intestinal microflora antibodies indicate a food allergy or food intolerance,
      (iii) higher than normal levels of both dietary antigen antibodies and intestinal microflora antibodies indicate a gut barrier dysfunction, and
      (iv) lower than normal levels of dietary antigen antibodies and microflora antibodies indicate a humoral immunodeficiency.

2. The method of claim 1, wherein step (b) comprises determining a level of antibodies against antigens of microorganisms found in normal intestinal microflora selected from the group consisting of yeast and bacteria.

3. The method of claim 2, wherein the microorganisms are bacteria selected from the group consisting of aerobic bacteria and anaerobic bacteria.

4. The method of claim 1, wherein determining the level of antibodies in either or both of steps (a) and (b) is accomplished using an ELISA test.

5. The method of claim 1, wherein the antibodies in either or both of steps (a) and (b) consist essentially of IgA.

6. The method of claim 4, wherein the antigens to normal intestinal microflora and/or dietary antigens are attached to a solid surface.

7. The method of claim 1, wherein the digestive disorders are selected from the group consisting of food allergy or intolerance, intestinal microflora imbalance, gut barrier dysfunction, bacterial translocation, and candidiasis.

8. The method of claim 2, wherein the microorganisms are yeast selected from the group consisting of *C. albicans, C. tropicalis*, and *C. cruzei*.

9. The method of claim 3, wherein the microorganisms are aerobic bacteria selected from the group consisting of *E. coli*, Lactobacillus species, and Enterococcus species.

10. The method of claim 3, wherein the microorganisms are anaerobic bacteria selected from the group consisting of *Bacteroides fragilis*, and *C. perfringens*.

11. The method of claim 1, wherein the dietary antigens are selected from the group consisting of wheat protein, soy, corn, milk, egg, and meat.

12. The method of claim 11, wherein the wheat protein is gliadin or gluten.

13. The method of claim 1 wherein the mucosal secretion in both steps (a) and (b) is saliva.

14. A method for determining the presence of digestive disorders in a patient, comprising:
   (a) determining a level of secretory IgA in a mucosal secretion sample from said patient;
   (b) comparing the level determined in step (a) with normal levels of said antibodies, wherein
      (i) lower than normal levels of secretory IgA indicates mucosal immunodeficiency and lack of immune reaction to antigens; and
      (ii) higher than normal levels of secretory IgA indicates an exposure of mucosal cells to significant levels of antigens.

15. The method of claim 14, wherein the antigens of (i) and (ii) are selected from the group consisting of dietary proteins, yeast, aerobic bacteria, and anaerobic bacteria.

16. The method of claim 14, further comprising
   (a) determining a level of antibodies against a dietary antigen in a first sample of a mucosal secretion from said patient;
   (b) determining a level of antibodies against a microorganism found in normal intestinal microflora in a second sample of a mucosal secretion from said patient, wherein first and second samples are the same or different,
   (c) comparing the levels determined in steps (a) and (b) with normal levels of said antibodies, wherein
      (i) higher than normal levels of intestinal microflora antibodies and normal levels of dietary antigen antibodies indicate an intestinal microflora imbalance,
      (ii) higher than normal levels of dietary antigen antibodies and normal levels of intestinal microflora antibodies indicate a food allergy or food intolerance,
      (iii) higher than normal levels of both dietary antigen antibodies and intestinal microflora antibodies indicate a gut barrier dysfunction, and
      (iv) lower than normal levels of dietary antigen antibodies and microflora antibodies indicate a humoral immunodeficiency.

17. The method of claim 14, further comprising determining a level of IgA, IgG, and IgM in a serum sample from said patient and comparing the level of serum IgA, IgG, and IgM from said patient with normal levels of said antibodies.

18. The method of claim 14, wherein the digestive disorders are selected from the group consisting of food allergy, candidiasis, microflora imbalance, intestinal barrier dysfunction, and humoral immunodeficiencies.

* * * * *